United States Patent [19]
Rey

[11] Patent Number: 5,503,618
[45] Date of Patent: Apr. 2, 1996

[54] HYDROMASSAGE PILLOW

[76] Inventor: Rafael R. Rey, 415 Hialeah Dr., Hialeah, Fla. 33010

[21] Appl. No.: 319,447

[22] Filed: Oct. 6, 1994

[51] Int. Cl.[6] .................................................. A61H 7/00
[52] U.S. Cl. ............................... 601/15; 601/148; 5/453; 5/933; 5/916
[58] Field of Search ..................... 601/148–150, 601/158, 15, 17, 56, 57, 154, 155, 158, 18; 5/644, 639, 453, 933, 916

[56] References Cited

U.S. PATENT DOCUMENTS

| | | | |
|---|---|---|---|
| 3,568,890 | 3/1971 | Leachman | 5/644 X |
| 3,613,671 | 10/1971 | Poor | 601/149 |
| 3,854,474 | 12/1974 | Carruth | 601/57 X |
| 3,981,032 | 9/1976 | Brooks | 5/639 |
| 4,607,405 | 8/1986 | Ellis et al. | 601/148 X |
| 4,635,619 | 1/1987 | Diamond | 601/148 |
| 4,635,620 | 1/1987 | Ricchio | 601/148 |
| 4,835,802 | 6/1989 | Purcey et al. | 601/148 X |
| 4,837,880 | 6/1989 | Coffman | 601/148 X |
| 4,839,930 | 6/1990 | Watkins | 601/148 X |
| 4,908,888 | 3/1990 | Watkins | 601/148 X |
| 5,016,618 | 5/1991 | Simmons | 601/148 |
| 5,020,517 | 6/1991 | Foster, Jr. et al. | 601/57 |
| 5,068,933 | 12/1991 | Sexton | 5/644 |
| 5,074,286 | 12/1991 | Gillaspie et al. | 601/148 |
| 5,188,096 | 2/1993 | Yoo | 601/57 |

*Primary Examiner*—Robert A. Hafer
*Assistant Examiner*—Brian E. Hanlon
*Attorney, Agent, or Firm*—Michael I. Kroll

[57] ABSTRACT

A hydromassage pillow comprising a sealed hollow cushion filled with water for placement under a head and neck, or lower back of a person. A framework is within the sealed hollow cushion. An assembly is coupled to the framework, for heating and pulsating the water within the sealed hollow cushion to provide a warm water jet-type massage to the head and neck, or lower back of the person resting on the sealed hollow cushion, so as to relieve muscle tension by greatly reducing and in some circumstances eliminating low back pain, neck pain and a headache in the person.

1 Claim, 2 Drawing Sheets

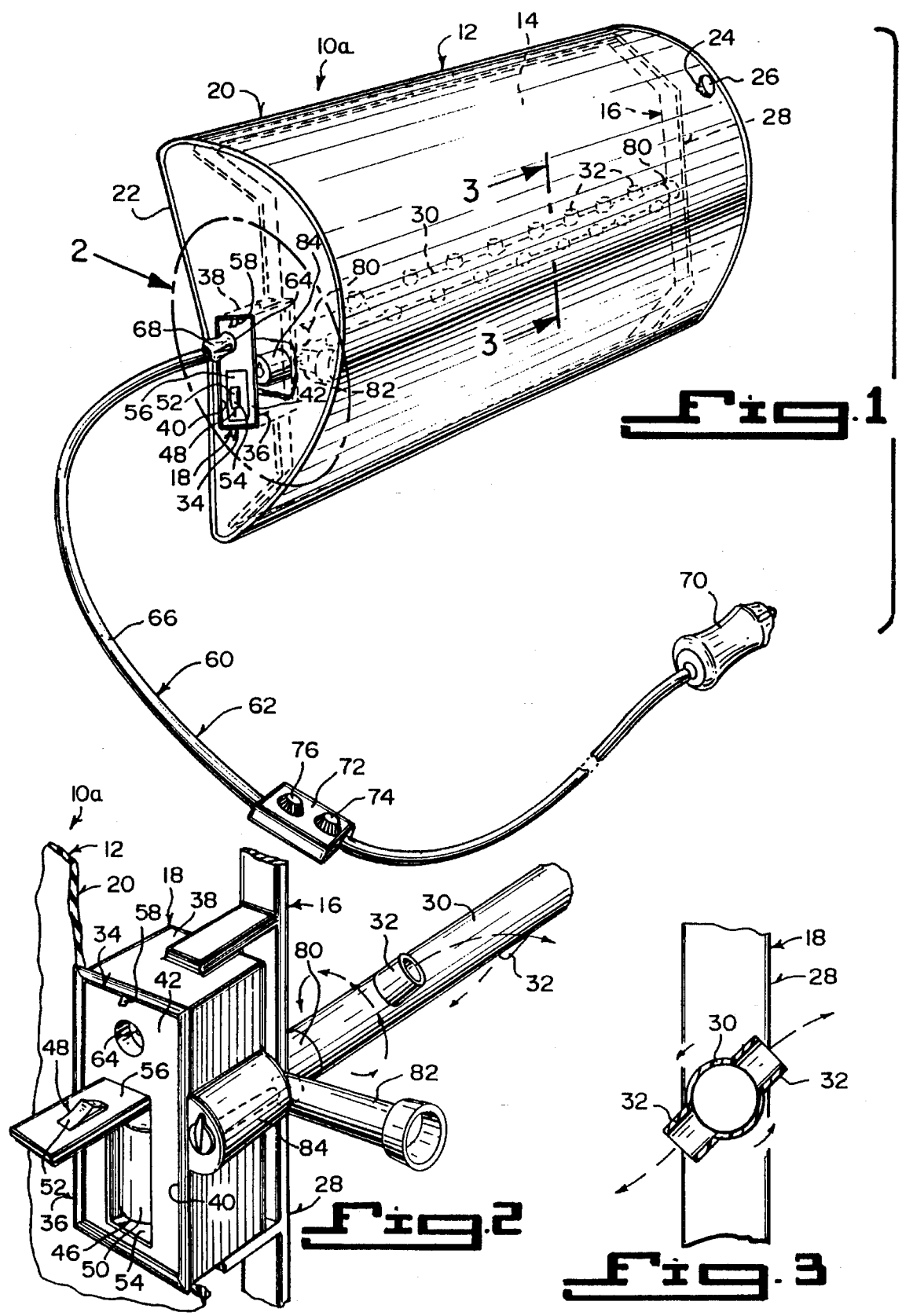

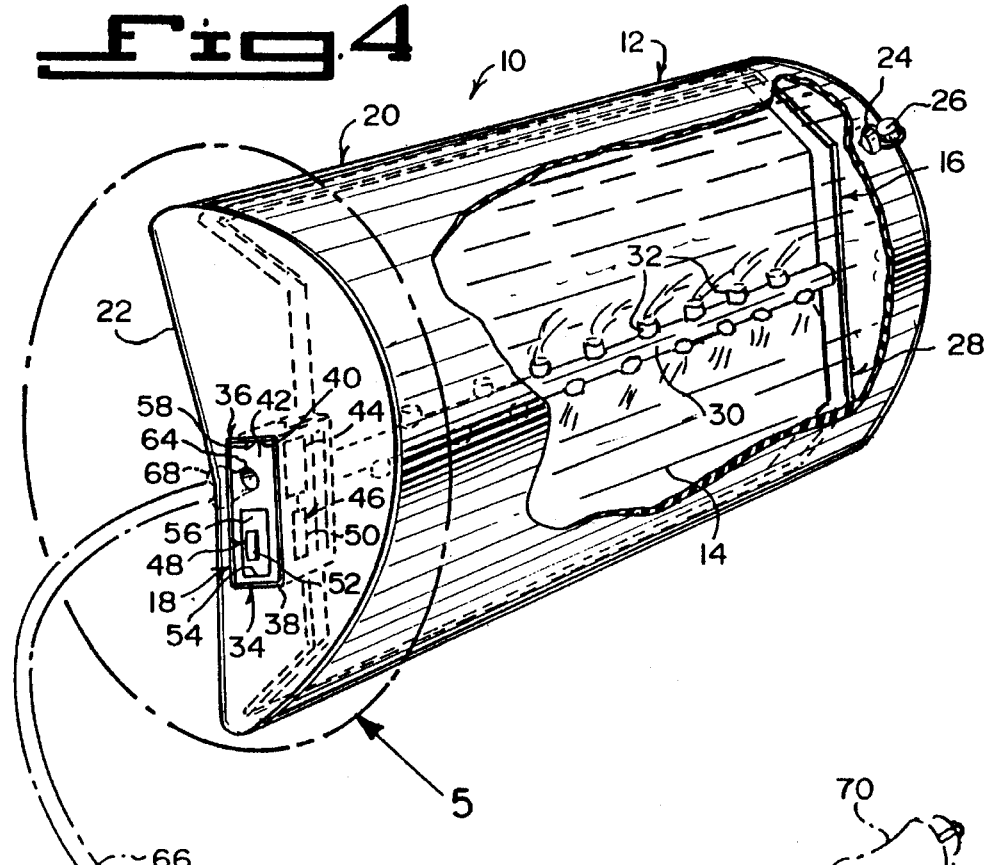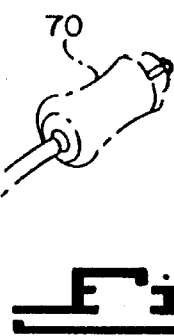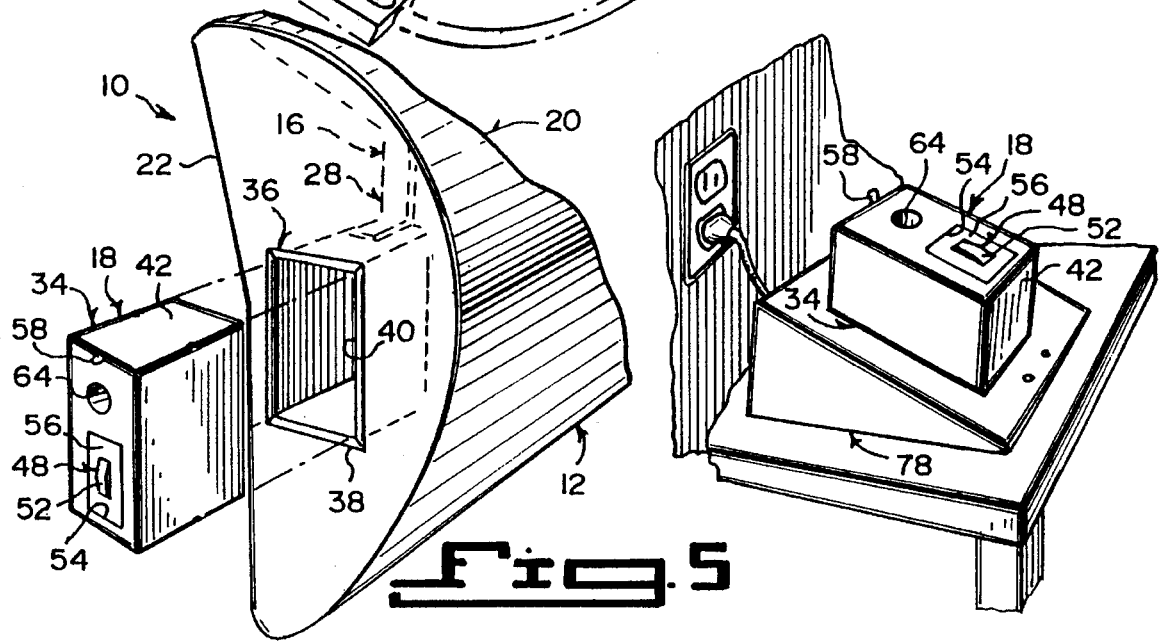

HYDROMASSAGE PILLOW

BACKGROUND OF THE INVENTION

1. Field of the Invention

The instant invention relates generally to head and neck, and lower back cushions and more specifically it relates to a hydromassage pillow.

2. Description of the Prior Art

Numerous head and neck, and lower back cushions have been provided in prior art. For example, U.S. Pat. No. 4,277,859 to Seaman; U.S. Pat. No. 4,887,326 to O'Brien et al.; U.S. Pat. No. 5,184,365 to Stafford and U.S. Pat. No. 525,429 to Genis all are illustrative of such prior art. While these units may be suitable for the particular purpose to which they address, they would not be as suitable for the purposes of the present invention as heretofore described.

A traveling pillow is described including an inner rubber inflatable pillow, an intermediate fiber-filled case for the pillow, and an exterior slip cover having a carrying handle. The carrying handle is provided with a compartment for storage of a small pneumatic pump for the inflatable pillow. A compact carrying case is also provided to store and carry the pillow in a deflated rolled-up form.

A suboccipital pillow for applying hot and/or cold treatments to the neck and suboccipital areas is provided, having a generally crescent shape. One side is fitted with a lightly insulated pocket. The other side is fitted with a heavily insulated pocket. The pillow is filled with a soft cushion, such as a polyester fiber batting. Both pockets have triangular tongues attached to their open sides. The tongues overlap and attach one to the other via a suitable fastener. A crescent shaped gel pack is provided which may either be cooled in a refrigerator or freezer or heated in boiling water or in a microwave over. After the gel pack has reached the desired temperature, it is inserted in the appropriate pocket. The pocket is closed by overlapping and fastening the two tongues.

A positioning system provides for airway management of a supine subject. A number of bags are provided for supporting the head and lower neck/upper shoulders area of the subject. Once the bags are positioned under the subject, each bag is pressurized using a pressurized fluid source which is controlled by a mechanical controller. The mechanical controller comprises a number of mechanical switches for regulating the pressure in each bag. By manipulating the mechanical switches, the pressure in each bag is adjusted to align the subject's head and lower neck/upper shoulders area such that the mouth, pharynx and trachea are linearly aligned.

A therapeutic rest is disclosed having a first pillow composed of a soft tufted cover filled with a cushion material. A second pillow composed of a soft flexible material is intended to be filled with a liquid of suitable temperature. A removable valve is incorporated into the second pillow for introducing the liquid into and out of the second pillow. The first and second pillows are of a U-shaped configuration. Releasable retainers are carried on opposing exterior surfaces of the pillows to permit attachment of the pillows when the pillows are in aligned U-shaped configuration.

SUMMARY OF THE INVENTION

A primary object of the present invention is to provide a hydromassage pillow that will overcome the shortcomings of the prior art devices.

Another object is to provide a hydromassage pillow that will relieve muscle tension with a warm water jet-type massage, so as to greatly reduce or in some circumstances eliminate low back pain, neck pain and headaches.

An additional object is to provide a hydromassage pillow that is compact and light weighted, so that it can be carried wherever a person will go, such as in an automobile, an airplane, on a trip, at work, at home, on long appointments and events.

A further object is to provide a hydromassage pillow that is simple and easy to use.

A still further object is to provide a hydromassage pillow that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein:

FIG. 1 is a perspective view of a first embodiment of the instant invention.

FIG. 2 is an enlarged perspective view as indicated by arrow 2 in FIG. 1, with parts broken away.

FIG. 3 is an enlarged cross sectional view taken along line 3—3 in FIG. 1.

FIG. 4 is a perspective view of a second embodiment of the instant invention with parts broken away and in phantom lines.

FIG. 5 is an enlarged perspective view as indicated by arrow 5 in FIG. 4, with the heater-pump unit exploded therefrom.

FIG. 6 is a perspective view showing a battery charger charging a battery within the heater-pump unit thereon.

Similar reference characters denote corresponding features consistently throughout the attached drawings.

DETAILED DESCRIPTION OF THE PREFERRED EMBODIMENTS

Turning now descriptively to the drawings, in which similar reference characters denote similar elements throughout the several views, FIGS. 4 and 5 illustrate a hydromassage pillow 10 comprising a sealed hollow cushion 12 filled with water 14 for placement under a head and neck, or lower back of a person. A framework 16 is within the sealed hollow cushion 12. An assembly 18 is coupled to the framework, for heating and pulsating the water 14 within the sealed hollow cushion 12 to provide a warm water jet-type massage to the head and neck, or lower back of the person resting on the sealed hollow cushion 12, so as to relieve muscle tension by greatly reducing and in some circumstances eliminating low back pain, neck pain and a headache in the person.

The sealed hollow cushion 12 is a durable inflatable plastic bag 20 to hold the water 14 therein. The bag 20 has a slightly elevated rear portion 22. The bag 20 has an access port 24. A removable cap 26 is to close off the access port 24, so that water can be added and removed. A conditioner can be added through the access port 24 for maintenance when needed.

The framework 16 is a flat stiffener member 28, which extends about an interior perimeter of the bag 20, so as to keep the bag 20 in its proper shape. The heating and pulsating assembly 18 consists of an elongated water pipe 30 extending horizontally between opposite sides of the flat stiffener member 28. A plurality of water jets 32 are along the water pipe 30. A heater-pump unit 34 is provided. A structure 36 is for coupling in a removable manner the heater-pump unit 34 to one end of the water pipe 30 through one side of the bag 20 and one side of the flat stiffener member 28. The heater-pump unit 34 will cause the water 14 to be heated up and pulsated when ejected through the water jets 32 within the bag 20.

The coupling structure 36 is a sleeve 38 having a side opening 40. The sleeve 38 is secured to one side of the flat stiffener member 28. The side opening 40 is located flush at one side of the bag 20. The sleeve 38 can receive the heater-pump unit 34 through the side opening 40.

The heater-pump unit 34 consists of a housing 42 with a heater-pump mechanism 44 therein, sized and shaped to fit into the sleeve 38 through the side opening 40. A power source 46 is electrically connected to the heater-pump mechanism 44 in the housing 42 to operate same. A component 48 is for turning the power source 46 on and off. The power source 46 is a battery. The on and off turning component 48 is an electrical switch 52.

The housing 42 has a compartment 54 for retaining the battery 50 in an electrical hook up to the heater-pump mechanism 44. A door 56 is for the compartment 54. The electrical switch 52 is built into the door 56. Access can be made into the compartment 54 when the door 56 is opened. A latch clip 58 is on the housing 42 to maintain the housing 42 to the sleeve 38 when inserted therein.

A facility 60 is for supplying an auxiliary power source to the heater-pump unit 34, to replace the battery when electrical power is required for long periods of time. The auxiliary power source supplying facility 60 is a cigarette lighter adapter 62 including the housing 42 of the heater-pump unit 34 having an electrical socket 64 therein. An elongated electrical cord 66 is provided. A first plug 68 is on a first end of the cord 66 to engage with the socket 64 in the housing 42. A second plug 70 is on a second end of the cord 66, to engage with a cigarette lighter socket in a dashboard of a motor vehicle. A controller 72 in the cord 66 has a first dial 74, for turning on and off the auxiliary power source and a second dial 76 for adjusting heat to the heater-pump mechanism 44 in the heater-pump unit 34. A remote battery charger 78 is shown in FIG. 6, to recharge the battery 50 within the heater-pump unit 34 when the battery 50 becomes discharged during use.

A modified hydromassage pillow 10a, shown in FIGS. 1 and 2, further includes a pair of bearings 80. Each bearing 80 is located at one end of the elongated water pipe 30 on one side of the flat stiffener member 28. When the water 14 is ejected through the water jets 32, the elongated water pipe 30 will rotate thereabout. A water return conduit 82 is fluidly coupled into one bearing 80 at one side of the flat stiffener member 28. An adjustable pulsation control mechanism 84 is on a side of the sleeve 38 transversely in engagement with the water return conduit 82.

LIST OF REFERENCE NUMBERS 10 hydromassage pillow
10a modified hydromassage pillow
12 sealed hollow cushion
14 water in 12
16 framework in 12
18 heating and pulsating assembly
20 durable inflatable plastic bag for 12
22 slightly elevated rear portion of 20
24 access part in 20
26 removable cap on 24
28 flat stiffener member for 16
30 elongated water pipe
32 water jet on 30
34 heater-pump unit
36 coupling structure
38 sleeve
40 side opening in 38
42 housing of 34
44 heater-pump mechanism in 42
46 power source in 42
48 on and off turning component
50 battery for 46
52 electrical switch for 48
54 compartment in 42 for 50
56 door
58 latch clip
60 auxiliary power source supplying facility
62 cigarette lighter adapter for 60
64 electrical socket in 42
66 elongated electrical cord
68 first plug on 66
70 second plug on 66
72 controller in 66
74 first dial on 72
76 second dial on 72
78 battery charger
80 bearing on 30 at 28
82 water return conduit on 80
84 adjustable pulsation control mechanism It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A compact and readily carried hydromassage pillow comprising:
  a) a sealed cushion containing a durable inflatable plastic bag filled with water for placement under a head and neck, or lower back of a person, said bag having a slightly elevated rear portion and an access port with a removable cap to permit water to be added or withdrawn from said bag and conditioner to be added for maintenance when needed;

b) a framework means within said sealed cushion comprising a flat stiffener member extending about an interior perimeter of said bag to maintain said bag in a predetermined shape;

c) means comprising a heater-pump unit for heating and pulsating the water within said sealed cushion to provide a warm water jet-type massage to the head and neck, or lower back of the person resting on said sealed cushion;

d) said heating and pulsating means including an elongated water pipe extending horizontally between opposite sides of said flat stiffener member, a plurality of water jets along said water pipe, said heater-pump unit heating, pumping and pulsating said water through said jets, said water pipe mounted on bearings to permit rotation about the longitudinal axis of the pipe so that when the water is ejected through said water jets said elongated water pipe will rotate directing the pulsating water jets to all of the pillow surfaces surrounding said water pipe; and e) means within one side of said plastic bag for coupling in a removable manner said heater-pump unit to one end of said water pipe comprising a sleeve having a side opening for receiving said heater-pump unit, said heater-pump unit including battery means and an auxiliary power source to substitute for said batter means when electrical power is required for long periods of time.

* * * * *